US011197708B2

(12) United States Patent
Cheng

(10) Patent No.: US 11,197,708 B2
(45) Date of Patent: Dec. 14, 2021

(54) PLASMA GENERATOR CONFIGURED FOR USE WITH AN AUXILIARY DEVICE

(71) Applicant: Gyrus ACMI, Inc., Southborough, MA (US)

(72) Inventor: Ming J. Cheng, West Warwick, RI (US)

(73) Assignee: Gyrus Acmi, Inc., Westborough, MA (US)

(*) Notice: Subject to any disclaimer, the term of this patent is extended or adjusted under 35 U.S.C. 154(b) by 341 days.

(21) Appl. No.: 15/908,000

(22) Filed: Feb. 28, 2018

(65) Prior Publication Data

US 2019/0262058 A1 Aug. 29, 2019

(51) Int. Cl.
*A61B 18/14* (2006.01)
*A61B 18/04* (2006.01)
(Continued)

(52) U.S. Cl.
CPC ........ *A61B 18/042* (2013.01); *A61B 1/00087* (2013.01); *A61B 18/1206* (2013.01); *A61B 18/148* (2013.01); *H01J 37/32532* (2013.01); *H01J 37/32623* (2013.01); *H01J 37/32889* (2013.01); *A61B 1/0014* (2013.01);
(Continued)

(58) Field of Classification Search
CPC ............ H05H 2245/122; A61B 18/148; A61B 18/042; A61B 2018/122; A61B 2018/162; A61B 2018/00982; A61B 2018/0091; A61B 2018/1213; A61B 2018/00583; A61B 1/0014; A61B 18/1206; A61B 1/00087; A61B 2018/00589; H01J 37/32532; H01J 37/32889

USPC ........ 606/32–34, 40–42, 49, 50; 607/98, 99, 607/104, 105, 107, 113, 115, 116
See application file for complete search history.

(56) References Cited

U.S. PATENT DOCUMENTS

2005/0171528 A1* 8/2005 Sartor .................. A61B 18/042
606/41
2011/0022043 A1* 1/2011 Wandke .................. A61N 1/40
606/41
(Continued)

FOREIGN PATENT DOCUMENTS

| EP | 2591743 A1 | 5/2013 |
|---|---|---|
| EP | 3533378 A1 | 9/2019 |
| GB | 2547941 A | 9/2017 |

OTHER PUBLICATIONS

Extended European Search Report for European Application No. 19156286.7, dated Aug. 7, 2019, 9 pages.
(Continued)

*Primary Examiner* — Thomas A Giuliani
(74) *Attorney, Agent, or Firm* — Schwegman Lundberg & Woessner, P.A.

(57) ABSTRACT

A plasma generator is described comprising an elongate member having a distal end, a proximal end, and a lumen extending therethrough, the proximal end configured to be connectable to a source of an inert gas, a plasma generation tip disposed at the distal end of the elongate member, the plasma generation tip configured to be in electrical communication with a power source, and an activation switch configured to control generation of plasma at the plasma generation tip, wherein the plasma generator is configured to be operably connectable to a medical device.

21 Claims, 7 Drawing Sheets

(51) Int. Cl.
  *H01J 37/32* (2006.01)
  *A61B 1/00* (2006.01)
  *A61B 18/12* (2006.01)
  *A61B 17/00* (2006.01)
  *A61B 18/00* (2006.01)
  *A61B 18/16* (2006.01)

(52) U.S. Cl.
  CPC ............... *A61B 2017/0023* (2013.01); *A61B 2018/0091* (2013.01); *A61B 2018/00583* (2013.01); *A61B 2018/00589* (2013.01); *A61B 2018/00982* (2013.01); *A61B 2018/1213* (2013.01); *A61B 2018/162* (2013.01)

(56) References Cited

U.S. PATENT DOCUMENTS

| | | | |
|---|---|---|---|
| 2012/0215158 A1* | 8/2012 | Barthel | A61B 18/042 604/26 |
| 2014/0074090 A1* | 3/2014 | Lam | A61B 18/042 606/49 |
| 2014/0228833 A1 | 8/2014 | Friedrichs et al. | |
| 2014/0309683 A1* | 10/2014 | Bagwell | A61B 18/1492 606/207 |
| 2015/0209098 A1* | 7/2015 | Shilev | A61B 18/042 606/42 |
| 2015/0238248 A1 | 8/2015 | Thompson et al. | |
| 2016/0121134 A1* | 5/2016 | Kalghatgi | A61N 1/44 604/23 |
| 2016/0220100 A1 | 8/2016 | Cheng et al. | |
| 2017/0071652 A1* | 3/2017 | Enderle | A61B 18/042 |
| 2017/0224197 A1 | 8/2017 | Green et al. | |
| 2017/0224404 A1* | 8/2017 | Sartor | A61B 17/00234 |
| 2017/0354453 A1* | 12/2017 | Krasik | A61B 1/018 |
| 2019/0380764 A1* | 12/2019 | Canady | A61B 18/042 |

OTHER PUBLICATIONS

"European Application Serial No. 19156286.7, Response filed Feb. 28, 2020 to Extended European Search Report dated Aug. 7, 2019", 6 pgs.

* cited by examiner

PLASMA GENERATOR CONFIGURED FOR USE WITH AN AUXILIARY DEVICE

FIELD OF THE DISCLOSURE

The embodiments of the present disclosure relate generally to a medical device. More particularly, the embodiments of the present disclosure relate to plasma generator which can be mechanically connected with an auxiliary device.

BACKGROUND

Endoscopes are typically used for minimally invasive surgery or to provide visual access to an internal location of a patient during a medical procedure. Endoscopes, during use, may be inserted into a location that may include tissue in need of coagulation, for example, following cutting using a surgical instrument. Additionally, endoscopes, during use, may be inserted into a location that may include debris that may cover a distal end of the endoscope and especially cover an imaging device located at the end of the endoscope. For example, an endoscope being used for surgery may become covered by blood and the blood may impair the vision of a surgeon so that surgery becomes increasingly difficult. Various devices and systems to assist a surgeon in clearing debris from the imaging device of the endoscope and restore vision may have features that attempt to control the flow of fluid, suction, or both at the end of the endoscope in an attempt to clear blood, debris, spots, droplets, or a combination thereof from the endoscope. Further, some of the endoscope systems leave droplets on the imaging device and/or lens and these droplets may inhibit vision through the lens and/or imaging device.

Coagulation, or clotting, is the process by which blood changes from a liquid to a gel, forming a blood clot. It potentially results in hemostasis, the cessation of blood loss from a damaged vessel, followed by repair. The natural mechanism of coagulation involves activation, adhesion, and aggregation of platelets along with deposition and maturation of fibrin. Encouraging coagulation through the use of medical devices is one way to clear the visual field of an endoscope.

Existing debriders apply radiofrequency (RF) technology to provide blood coagulation during treatment. Some problems may arise in coagulation using this method. For example, tissue may stick easily to the debrider, resulting in tissue charring; the debrider may be likely to overheat at the distal tip or elsewhere; the distal tip has to be wiped frequently during operation after charring has occurred; and the RF bipolar feature adds complexity to the design of the debrider instrument.

SUMMARY

It would be advantageous in view of the above discussion to provide an improved system for minimizing blood or other fluids clouding the field of view of a region of interest. It would be advantageous in view of the above discussion to provide systems and methods for a plasma gun, operable under high frequencies that may be attached to an endoscope for use inside a subject's anatomy. It would be advantageous in view of the above discussion to provide systems and methods for a plasma gun that is configured to coagulate blood and minimize disruptions to the field of view of an endoscope. It would be advantageous in view of the above discussion to provide systems and methods for a plasma gun that may be connected to an endoscope via a clip system.

The present disclosure provides an improved plasma gun device configured for coagulation and/or killing bacteria via delivery of a plasma plume. As used herein, coagulation may be defined as the action or process of a liquid, especially blood, changing to a solid or semi-solid state. Plasma, as used herein, may be defined as a substance whose usage describes the behavior of ionized atomic nuclei and electrons within the surrounding region of the plasma. Plasma, as used herein, may be defined as a state of matter in which an ionized gaseous substance becomes highly electrically conductive to the point that long-range electric and magnetic fields dominate the behavior of the matter. As used herein, a plasma plume may be defined as a mass or stream of plasma that extends from the tip of the device. The present disclosure provides a plasma gun device configured for non-contact treatment. The present disclosure provides a plasma gun device configured for use with high frequencies. In some embodiments, the present disclosure provides a plasma gun device that may be disposable. In some embodiments, the present disclosure provides a plasma gun that may be reusable and sterilized for reuse.

Another possible embodiment of the present teachings comprises a method comprising (1) connecting a sheath to an endoscope; (2) connecting a delivery line containing an inert gas to the sheath; (3) connecting an active electrode and a return electrode to a generator; and (4) controlling a frequency of operation and/or the flow of inert gas to a distal tip for creation of a plasma plume.

The teachings herein provide a plasma gun device that may be configured with an endoscope system that may be further configured with a lens cleaning device. The teachings herein provide an endoscope system that washes an endoscope lens and/or imaging device including a plasma gun device and may be further configured to remove all debris and fluid droplets so that vision is not impaired. The teachings herein provide a method of clearing a visual field of an endoscope where the firing of a plasma gun device is triggered by a single action. The teachings herein provide a plasma gun system that is controlled by a foot system.

Accordingly, pursuant to one aspect of the present invention, there is contemplated a plasma generator, comprising an elongate member having a distal end, a proximal end, and a lumen extending therethrough, the proximal end configured to be connectable to a source of an inert gas, a plasma generation tip disposed at the distal end of the elongate member, the plasma generation tip configured to be in electrical communication with a power source, and an activation switch configured to control generation of plasma at the plasma generation tip, wherein the plasma generator is configured to be operably connectable to a medical device.

The disclosure may be further characterized by one or any combination of the features described herein, such as a first electrode and a second electrode, the first electrode is an active electrode and the second electrode is a return electrode, the plasma generation tip comprises stainless steel, a plasma plume is generated at the plasma generation tip extending between 20 mm and 50 mm in front of the distal tip of the plasma generator, the activation switch comprises a first control button and a second control button and the first control button controls release of an inert gas and the second control button controls current delivery to the elongate member, the first control button is configured to supply a burst of fluid or a continuous flow of fluid and further includes and a stop feature, the plasma generator is configured to be disposable, the medical device and the plasma generator are configured to be operated using a single hand of a user.

Pursuant to another aspect of the present disclosure, there is contemplated a medical device, comprising a plasma generator configured to be operably connectable to the medical device, wherein the plasma generator comprises an elongate member having a distal end, a proximal end, and a lumen extending therethrough, the proximal end configured to be connectable to a source of an inert gas, a plasma generation tip disposed at the distal end of the elongate member, the plasma generation tip configured to be in electrical communication with a generator; and an activation switch configured to control generation of plasma at the plasma generation tip.

The disclosure may be further characterized by one or any combination of the features described herein, such as a first electrode and a second electrode, the first electrode is an active electrode and the second electrode is a return electrode, the plasma generation tip comprises stainless steel, a plasma plume is generated at the plasma generation tip extending between 20 mm and 50 mm in front of the distal tip of the plasma generator, the plasma generator is configured for non-contact treatment, the plasma generator is configured to coagulate blood in the vicinity of the plasma generation tip, the plasma generator is configured to perform a disinfection function in the vicinity of the plasma generation tip, the activation switch comprises a first control button and a second control button and the first control button controls release of an inert gas and the second control button controls current delivery to the elongate member, the plasma generator is configured to be disposable, the medical device and the plasma generator are configured to be operated using a single hand of a user.

The claimed subject matter is not intended to be limited to a composition or method that must satisfy one or more of any stated objects or features of the devices described herein. It is also important to note that the claimed subject matter is not limited to the exemplary or primary embodiments described herein. Modifications and substitutions by one of ordinary skill in the art are considered to be within the scope of the disclosure.

Further aspects, advantages, and areas of applicability will become apparent from the description provided herein. It should be understood that the description and specific examples are intended for purposes of illustration only and are not intended to limit the scope of the present disclosure.

Figure 1:
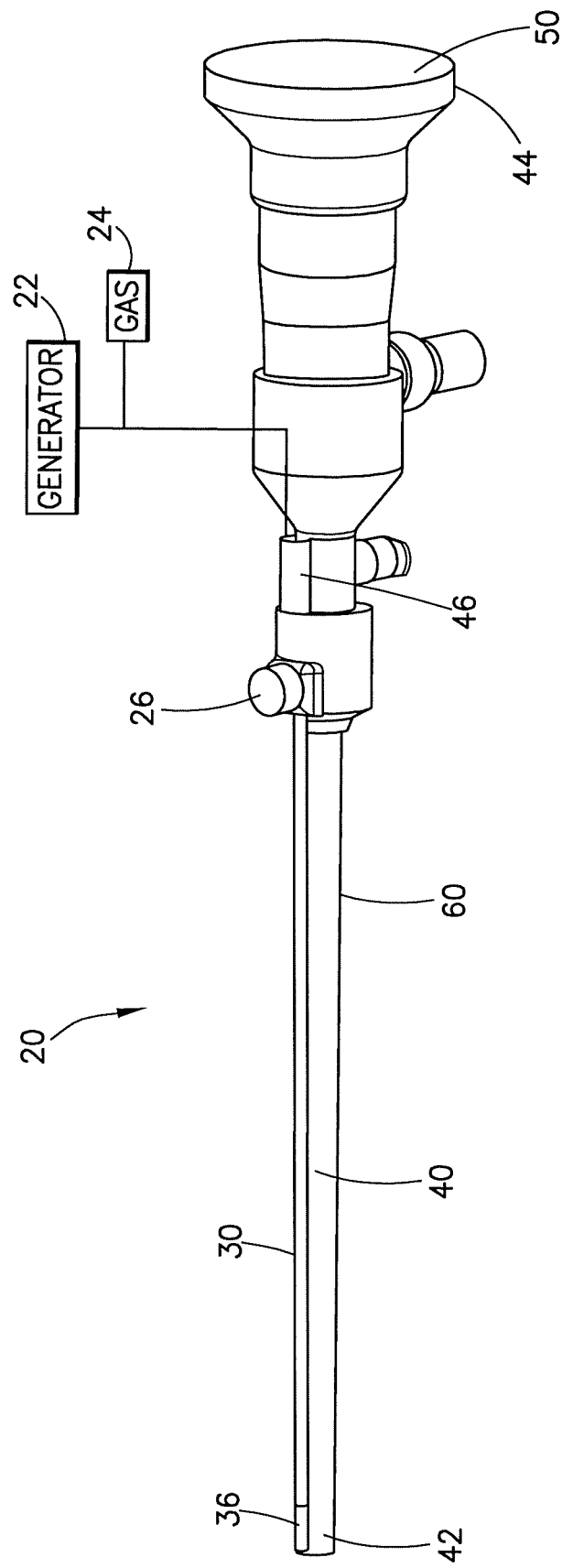
FIG. 1 illustrates a top rear perspective view of a plasma gun device, in accordance with one embodiment of the disclosure.

These and other features of the present embodiments will be understood better by reading the following detailed description, taken together with the figures herein described. The accompanying drawings are not intended to be drawn to scale. For purposes of clarity, not every component may be labeled in every drawing.

DETAILED DESCRIPTION

The explanations and illustrations presented herein are intended to acquaint other skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents of which such claims are entitled. The disclosure of all articles and references, including patent applications and publications, are incorporated by reference for all purposes. Other combinations are also possible as will be gleaned from the following claims, which are also hereby incorporated by reference into this written description.

The plasma generator system and associated methods described herein provide a plasma gun device which may be implemented independently or configured with an endoscope and/or a lens cleaning device.

In one embodiment, a plasma generator system is described that is configured to coagulate tissue and provide disinfection benefits to an anatomical region of interest. In one embodiment, a method for non-contact coagulation or disinfection treatment is provided. In one embodiment, a plasma gun system is provided that is configured for temperature adjustment. In one embodiment, a plasma gun system is provided which is configured to attach to an endoscope via a clip system. In one embodiment, an endoscope system is provided that is configured to coagulate tissue, provide disinfection benefits, wash an endoscope lens and/or imaging device and remove all debris and fluid droplets so that vision is not impaired. In one embodiment, a plasma gun device is provided that can be controlled via a foot system. In one embodiment, a plasma generator is provided that may be operated in combination with an auxiliary medical device using a single hand of a user.

The present teachings meet one or more of the present needs by providing: (1) an insulated sheath configured for receiving power from a power source; (2) a sheath configured for receiving an inert gas; (3) a distal tip for delivering inert gas to an anatomical region of interest; (3) electrode wires extending along the insulated sheath and connected to a generator; (4) a control module located between the sheath, the electrode wires, the source of insert gas, the generator to control the frequency of operation and the rate of flow of inert gas.

General Overview

Inert gases may be used with electrical energy provided from a power source for plasma generation. The system and methods described herein are configured to generate a plasma plume at a distal tip of a medical device. Delivery of plasma to a region of interest (i.e. tissue), may affect multiple properties of the region of interest. Plasmas have the unique ability to create large fluxes of radiation (i.e. ultraviolet), ions, photons, electrons, and other excited-state species which are suitable for performing material property changes with high spatial and material selectivity and temporal control. Plasmas may remove an upper layer of a region of interest with little or no effect on a separate underlayer or it may be used to selectively remove a particular region of tissue with minimal effect to adjacent tissue types. Plasmas are capable of modifying the chemical nature of tissue surfaces by breaking chemical bonds, for example. During plasma generation, each of the ionized atomic nuclei is suspended in a mobile sea of electrons. Some examples of insert gases that can be used for this purpose include argon gas and helium gas, or a combination thereof. The plasma generation device may be configured for operation with gas flow rates of between about 7 L/min and about 10 L/min for helium gas. Testing has found that helium gas has a lower ionized voltage breaking point, so it is more controllable and desirable regarding cold plasma treatment. Other inert gases, such as neon gas, krypton gas, xenon gas and radon gas, or a combination thereof, may also be used.

The power source may include any suitable components for delivering power or matching impedance to the plasma device. More particularly, the power source may be any radio frequency generator or other suitable power source capable of producing electrical power to ignite and sustain the ionizable media to generate a plasma plume. Plasma is generated using electrical energy that is delivered as either direct current (DC) electricity or alternating current (AC) electricity, in either continuous or pulsed modes. The plasma may also be ignited by using continuous or pulsed direct current (DC) electrical energy or continuous or pulsed RF electrical energy or combinations thereof. The plasma generation device may be configured for operation from between about 30 W and 120 W, between about 50 W and 100 W, or between about 60 W and 80 W. Electrical energy level may depend upon voltage, frequency, type of inert gas used and specific applications or desired use.

Input values for excitation frequency, operating voltage, and current levels, as well as phase affect the electron temperature and electron density. Further, choices of electrical excitation and plasma device hardware also determine how a given plasma system responds dynamically to the introduction of new ingredients to the host plasma gas or liquid media. In some embodiments, frequency, voltage, and current are user selectable. In some embodiments, frequency, voltage, and current are presets configured to maximize power transfer from the electrical circuit to the plasma. In some embodiments, the temperature of the generated plasma may be configurable by adjusting frequency and power settings.

Delivery of a plasma plume to an anatomical region of interest can provide coagulation benefits as well as serve to kill bacteria. During coagulation, modification of the surface of the tissue may require sputtering. Sputtering, as used herein, may be defined as a process whereby particles are ejected from a solid target material due to bombardment of the target by energetic particles, particularly inert gas ions. In some embodiments, argon gas may be used for sputtering as the argon ions have a high mass and there is no surface chemistry involved with argon.

In one aspect, the disclosure features an electrode configured to produce a plasma plume, or plasma arc torch when in contact with inert gas at or near a plasma generation tip. In one aspect, the disclosure features a plasma generator configured for non-contact treatment. A generated plasma plume may reach a target positioned between about 5 mm to about 70 mm, about 10 mm to about 60 mm, about 20 mm to 50 mm in front of the distal tip of the plasma generator. A generated plasma plume may extend a length of between about 5 mm to about 70 mm, about 10 mm to about 60 mm, about 20 mm to 50 mm in front of the distal tip of the plasma generator. The electrode comprises an elongated electrode body formed of a high thermal conductivity material. The material can be copper, silver, gold, platinum, or any other high thermal conductivity material with a high melting and boiling point and which is chemically inert in a reactive environment. The electrode may include wires 34 forming an active electrode and a return electrode.

In some embodiments, a plasma generator may be attached or configured to be attached to an auxiliary device, such as a medical device including an endoscope, a debrider, a lens cleaning device, or the like. In one aspect, the plasma generator may be configured to attach to an auxiliary device using a set of snap rings, a set of clips, or a sheath. In one aspect, the operational distal tips of the plasma generator and the auxiliary device are configured to be aligned. In one aspect, the plasma generator and the auxiliary device may be configured to be operable using a single hand of a user.

Figure 4:
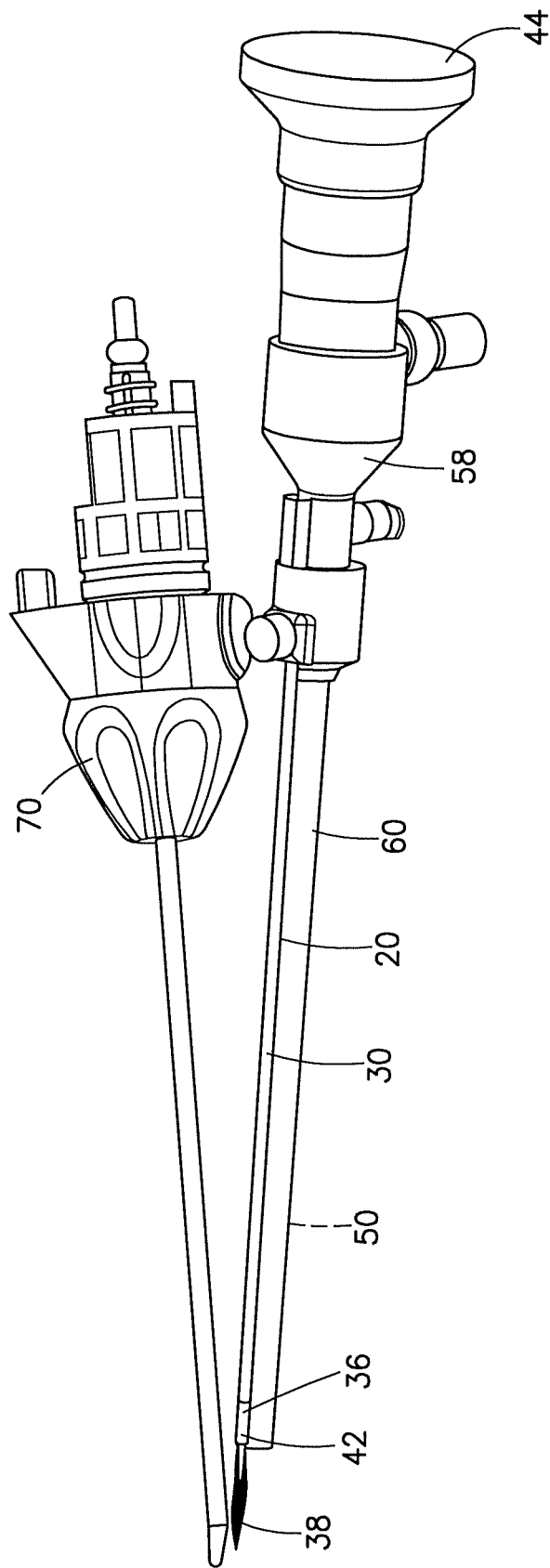
FIG. 4 illustrates a top rear perspective view of a plasma gun device and a debrider, in accordance with one embodiment of the disclosure.
Figure 5A:
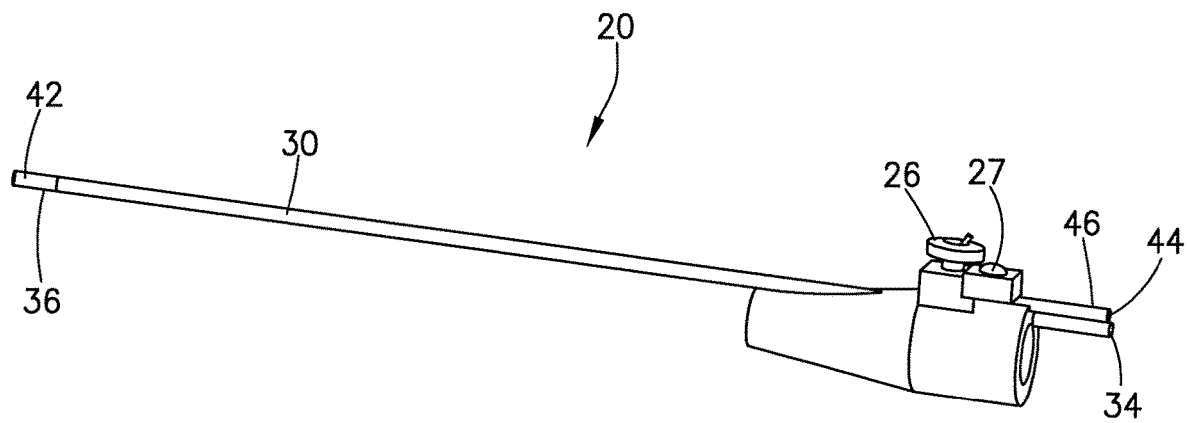
FIG. 5A illustrates a top rear perspective view of a standalone plasma gun device, in accordance with one embodiment of the disclosure.

Turning now to the drawings to illustrate examples of embodiments of the present teachings, in some embodiments, plasma generator 20 described herein may be a standalone device, as shown in FIG. 5A. In other embodiments, plasma generator 20 may be configured with an endoscope, as shown for example in FIGS. 1-4. In some embodiments, endoscope 60 may be configured with a lens cleaner device.

Structurally, in some embodiments, plasma generator 20 may be integrally formed along the length of a shaft of endoscope 60, as shown in FIG. 1. In other embodiments, plasma generator 20 may be threaded onto endoscope 60 using a set of snap rings 52, as shown in FIGS. 2A-3.

In one embodiment, shown in FIG. 1, insulated sheath 30 surrounds a tube which houses a connection to a generator 22 as well as lumen 46 for fluid communication with an inert gas 24. The tube may be a metal tube that extends along the length of plasma generator 22. The tube may have an outer diameter of between about 0.75 mm and 3.5 mm, between about 1.0 mm and 3.0 mm, or between about 1.5 mm and 2.0 mm. Plasma generation tip 36 is positioned at a distal end 42 of plasma generator 20. The tube and/or plasma generation tip 36 may comprise any metal that is heat resistant up to 100° C. that does not rust and that has superior electrical conductance, such as stainless steel, for example. Plasma generation tip 36 may be a portion of the stainless steel tube devoid of insulation at a distal end 42. Plasma generation tip 36 may be configured to be in electrical communication with a power source and in flow communication with a source of inert gas. Mixing of electrical energy from generator 22 with the inert gas 24 may occur along the length of insulated sheath 30, at plasma generation tip 36, or at a combination thereof.

An activation switch is provided with plasma generator 20. In some embodiments, the activation switch is a one-part activation switch, for example as shown in FIG. 1. In a one-part activation, control button 26 may function to simultaneously release inert gas into lumen 46 and pull power from generator 22. In other embodiments, the activation switch is a two-part activation switch. In a two-part activation, control button 26 may function to either release inert gas into lumen 46 or pull power from generator 22 and a second control button may perform the other function. Control button 26 may be a push button activation, where the normal state is OFF mode and the depressed state triggers the ON state.

Figure 2A:
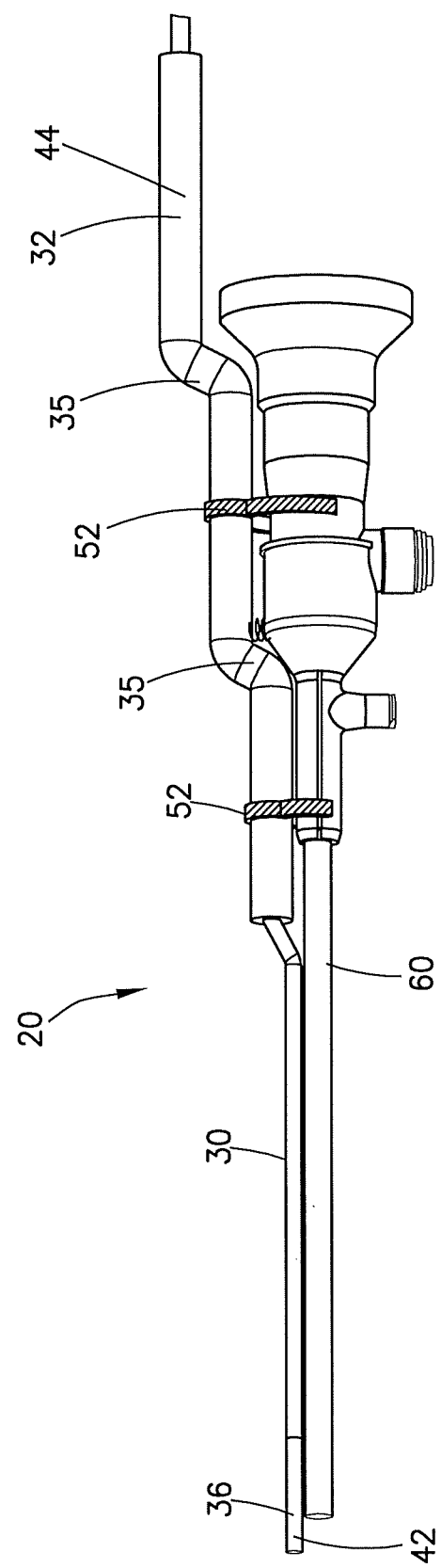
FIG. 2A illustrates a side view of a plasma gun device, in accordance with one embodiment of the disclosure.
Figure 2B:
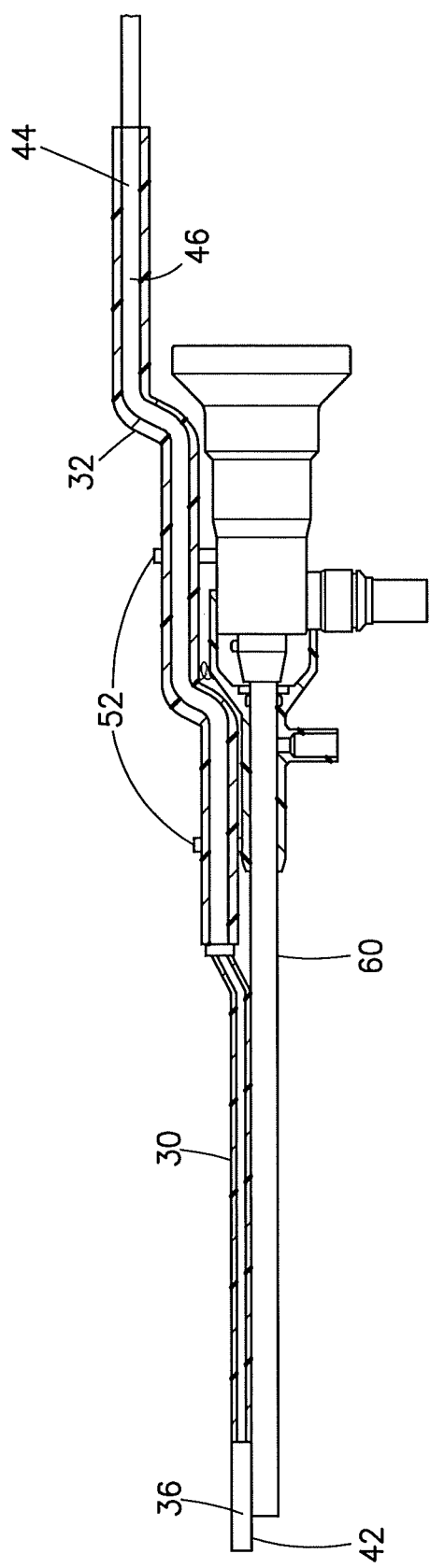
FIG. 2B illustrates a cross-sectional view of a plasma gun device, in accordance with one embodiment of the disclosure.
Figure 3:
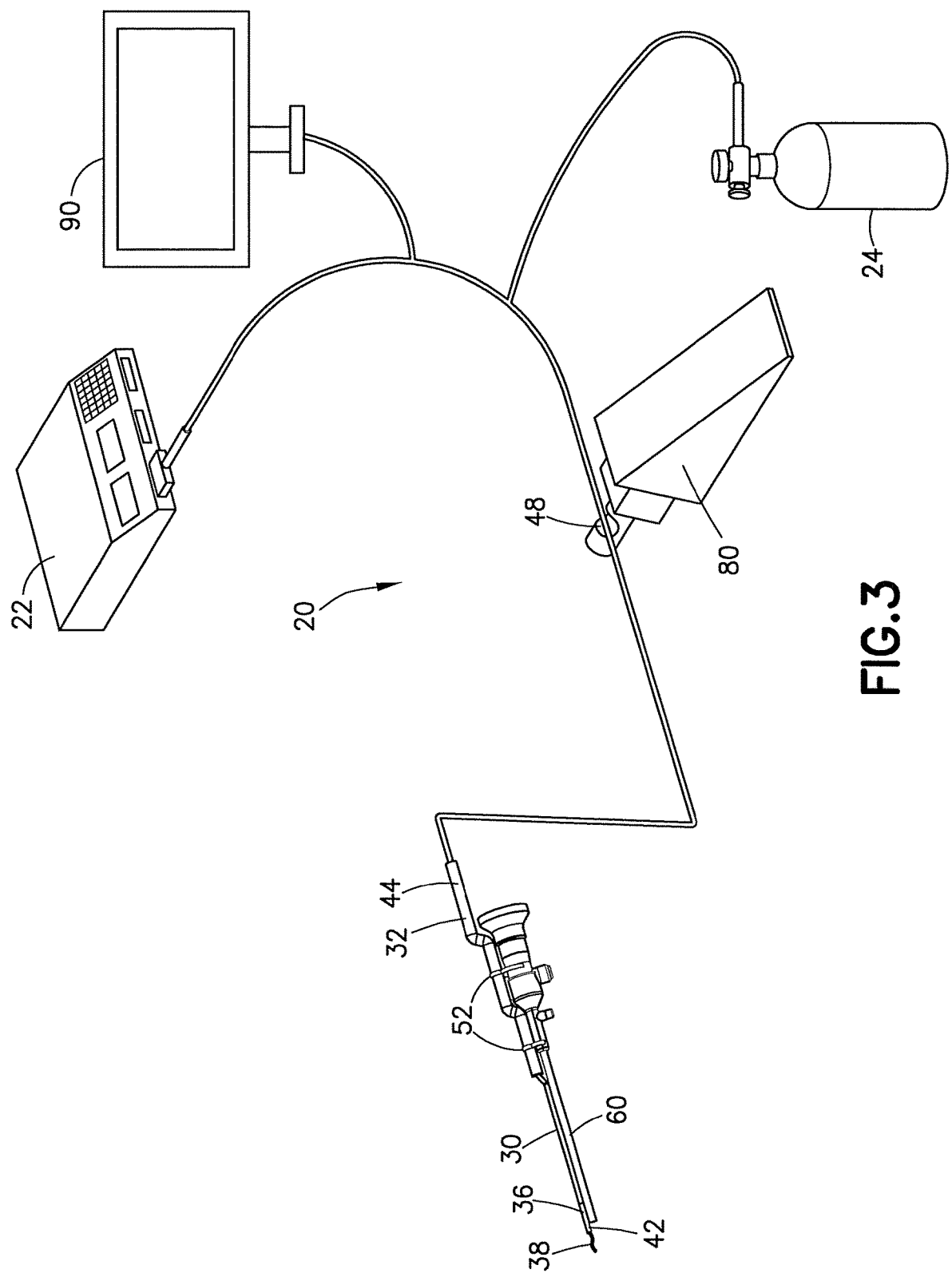
FIG. 3 illustrates a top front perspective view of a plasma gun device, in accordance with one embodiment of the disclosure.

In another embodiment, shown in FIGS. 2A-3, for example, insulated sheath 30 is contained at a proximal end by malleable sheath 32. Malleable sheath 32 extends to a rear or proximal end 44 of plasma generator 20 and is supported by a set of snap rings 52. In the illustrated embodiment, malleable sheath 32 follows the outer contour of endoscope 60 and has two distinct joint portions 35 along the length of malleable sheath 32. Joint portions 35 are sections of malleable sheath which have been bent first to an angle offset from the longitudinal axis and subsequently bent to follow the longitudinal axis of endoscope 60. Malleable sheath 32 can be formed of a soft bendable material, for example materials comprising a metal, including aluminum. Plasma generation tip 36 is positioned at a distal end 42 of plasma generator 20. Mixing of electrical energy from generator 22 with the inert gas 24 may occur along the length of insulated sheath 30, at plasma generation tip 36, or at a combination thereof. When the inert gas becomes electrified, electrons in the inert gas become excited and active and can destroy bacteria and/or coagulate blood.

FIG. 3 illustrates connections with footswitch or foot pedal 80 (via pinch value 48), a source of inert gas 24, generator 22, and a control monitor 90. Control monitor 90 may be used to control frequency, voltage, and/or current. Generator 22 may be an RF generator. Control monitor 90 may be configured with a central processing unit (CPU). A user may interact with control monitor 90 to determine what power settings may be ideal for a given operational scenario. A user may select power settings (frequency, voltage, and current levels) to ensure effective coagulation for a patient.

FIG. 4 illustrates an alternate embodiment where debrider 70 is configured to work alongside plasma generator 20. During operation, debrider or microdebrider 70 may cut tissue and cloud the visual field of an endoscope lens. Thus, it would be desirable to speed up the coagulation process through use of a plasma plume 38 from plasma generator 20 and minimize the flow of blood in the vicinity of the distal tip 42 of plasma generator 20. It would further be desirable to include lens cleaner 58 to clear any debris from the lens of endoscope 60 so that an anatomical region of interest can visualized clearly through optics 50. Lens cleaner 58 may include an irrigation line for supplying liquid at the endoscope lens and a suction line for clearing liquid from the endoscope lens.

In some examples, plasma generator 20 is configured to be operably engaged with lens cleaning devices described, for example in application Ser. No. 15/095,651, entitled ENDOSCOPE SYSTEM INCLUDING A RESILIENT RESERVOIR, filed Apr. 11, 2016, which is incorporated by reference herein in its entirety. In some examples, plasma generator 20 is configured to be operably engaged with lens cleaning devices described, for example in application Ser. No. 15/414,998, entitled ENDOSCOPE SYSTEMS INCLUDING DROP RETENTION FEATURES, filed Jan. 25, 2017, which is incorporated by reference herein in its entirety.

The lens cleaning device may include use of a sheath which may surround an endoscope, as well as an irrigation source and a suction source connected to the sheath. The lens cleaning device may include one or more functional components that may extend proximate to a distal end of an endoscope or beyond a distal end of an endoscope. The lens cleaning device may provide one or more conduits relative to the endoscope. The lens cleaning device may be configured to supply a burst of fluid or be configured with a continuous flow and a stop feature.

Figure 5B:
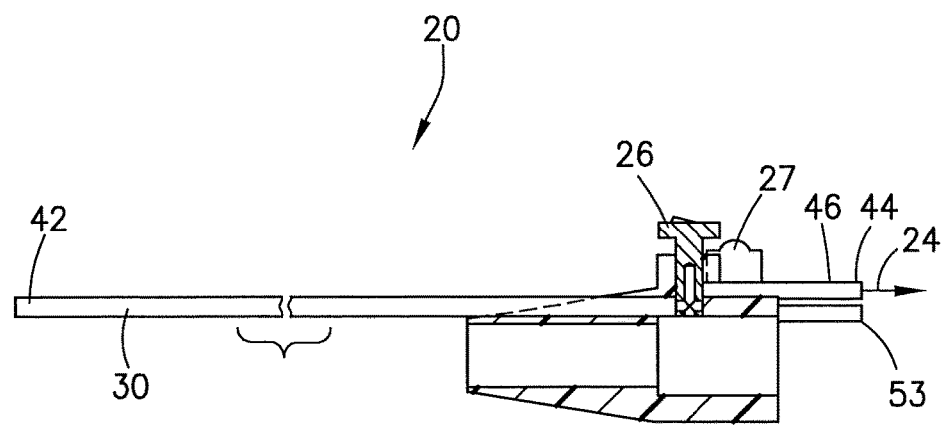
FIG. 5B illustrates a cross sectional view of a standalone plasma gun device, in accordance with one embodiment of the disclosure.

FIGS. 5A-5B illustrate a standalone plasma generator 20 comprising at least one electrode 53 and connection to a source of inert gas 24. Insulated sheath 30 houses a connection to a generator 22 (shown in FIG. 3) as well as lumen 46 for fluid communication with an inert gas 24. The illustrated embodiment includes a pair of control buttons 26, 27. Control button 26 may be configured to permit or restrict the flow of current from generator 22. Control button 27 may be configured to permit or restrict the flow of inert gas 24 via lumen 46. In alternate embodiments, the functions of control button 26 and control button 27 may be switched.

In the embodiments illustrated in FIGS. 5A-5B, a one-part activation switch may include control button 26 or control button 27. A two-part activation switch may include control button 26 and control button 27. A first step of the two-part activation may permit the flow of inert gas; a second step of the two part activation may permit the flow of current from generator 22. Control button 26, 27 may be a push button activator, where the normal state is OFF mode and the depressed state triggers the ON state. The control button designed to control the flow of inert gas may be configured to supply a burst of fluid or be configured with a continuous flow and a stop feature.

Figure 6:
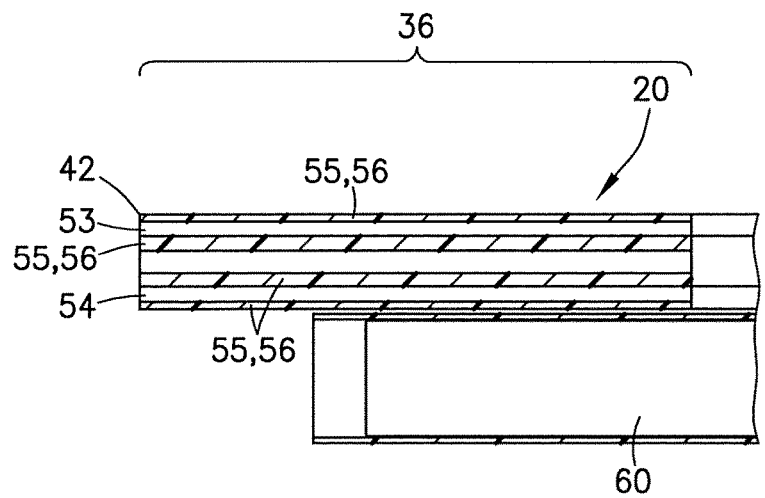
FIG. 6 illustrates a cross-sectional view a distal end of a plasma gun device, in accordance with one embodiment of the disclosure.
Figure 7:
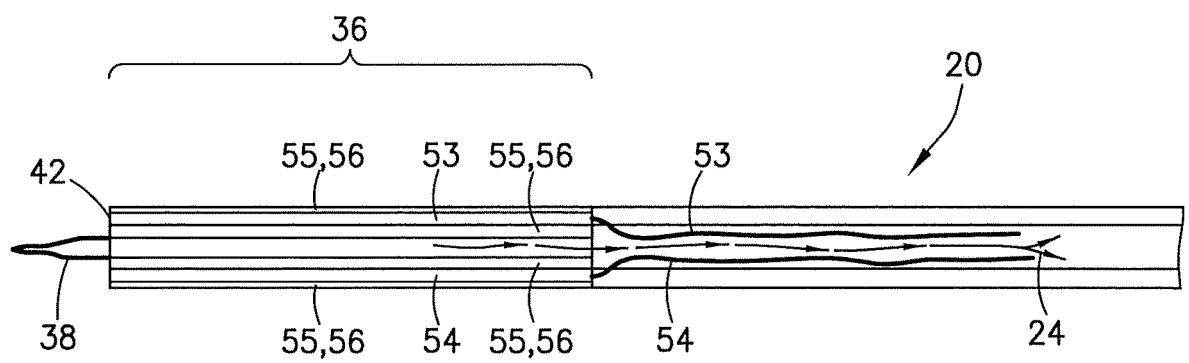
FIG. 7 illustrates a cross-sectional view of electrical and fluid communication in a distal portion of a plasma gun device, in accordance with one embodiment of the disclosure.

FIG. 6 illustrates a close up view of plasma generation tip 36 and a distal portion of insulated sheath for the embodiments shown in FIGS. 1-4, which also include the distal portion of endoscope 60. FIG. 7 illustrates a close up view of plasma generation tip 36 and a distal portion of insulated sheath 30 for the embodiments shown in FIGS. 5A-5B. In each of FIGS. 6-7, at distal end 42, plasma generation tip 36 houses active electrode 53 and return electrode 54. Each of active electrode 53 and return electrode 54 extend through an embedded lumen 56 in insulated sheath 30 at plasma generation tip 36 to deliver energy at distal tip 42 via plasma plume 38. Each embedded lumen 56 is surrounded with a layer of insulation 55. Mixing of electrical energy from generator 22 with the inert gas 24 may occur along the length of insulated sheath 30, at plasma generation tip 36, or at a combination thereof.

Functionally, plasma generator 20 may be configured to work over a frequency range of about 200 KHz to about 400 KHz. Plasma generator 20 may be targeted for operation under 100° C. Plasma generator 20 may be configured for coagulation, bacterial destruction, or other desired outcomes. Plasma generator 20 may be configured for non-contact treatment. Treatment may be accomplished via a plasma plume 38 that is emitted from plasma generation tip 36. Blood solidifies and coagulates upon encountering the high temperature plasma plume 38. The plasma plume may be delivered to a patient at a temperature of between 40° C. and 120° C., between 50° C. and 110° C., or between 60° C. and 100° C.

In alternate embodiments, connection to a source of inert gas 24 via lumen 46 and connection to generator 22 via electrodes 53, 54 may be integrally formed inside elongate member 40 of endoscope 60.

The return electrode may be coupled through an isolation transformer (not shown) disposed within generator 22 to provide electrical isolation. Each of the electrodes 53 and 54 is coupled to the generator 22 as a power source via leads. The generator 22 as the power source drives plasma generation such that the energy from the power source may be used to ignite the plasma feedstocks flowing through the device 12. In some embodiments, applied power to the electrodes 53 and 54 for generation of the plasma plume 38 may be from about 10 watts (W) to about 50 W. In some embodiments, applied power may be from about 20 W to about 30 W.

The plasma effluent to be delivered as plasma plume 38 may be generated at plasma generation tip 36 as inert gas passed between active electrode 53 and return electrode 54.

Although several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto; the details of the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

ELEMENT NUMBERS 20 plasma gun
22 generator
24 inert gas
26 control button
27 control button
30 insulated sheath
32 malleable sheath
34 wire
35 joint portion
36 plasma generation tip
38 plasma plume
40 elongate member
42 distal end
44 proximal end
46 lumen
48 pinch valve
50 optics
52 snap ring
53 active electrode
54 return electrode
55 insulation
56 embedded lumen
58 lens cleaner
60 endoscope
70 microdebrider
80 foot pedal
90 monitor

What is claimed is:

1. A plasma generator comprising:
an elongate member having a distal end, a proximal end, and a lumen extending therethrough, the proximal end configured to be connectable to a source of an inert gas, the elongate member comprising an insulated sheath;
a plasma generation tip disposed at the distal end of the elongate member, the plasma generation tip configured to be in electrical communication with a power source;
an activation switch configured to control generation of plasma at the plasma generation tip; and
a malleable sheath extending proximally from the proximal end of the elongate member, the lumen running through the malleable sheath, for flow of the inert gas therethrough, wherein the insulated sheath is encircled at the proximal end by the malleable sheath;
wherein the plasma generator is configured to be operably connectable to a medical device, wherein the malleable sheath is couplable to follow along a contour of the medical device, and
wherein the plasma generator comprises one or more rings configured to attach the malleable sheath to an exterior portion of the medical device and support the malleable sheath, the one or more rings configured to allow flow of the inert gas through the malleable sheath.

2. The plasma generator of claim 1, wherein the plasma generation tip comprises a first electrode and a second electrode, each of the first and second electrodes extending along the elongate member to the distal end, wherein the first electrode is an active electrode and the second electrode is a return electrode.

3. The plasma generator of claim 1, wherein the plasma generation tip is comprised of stainless steel.

4. The plasma generator of claim 1, wherein the plasma generator is configured to generate a plasma plume at the plasma generation tip extending between 20 mm and 50 mm in front of a distal end of the plasma generator.

5. The plasma generator of claim 1, wherein the activation switch comprises a first control button and a second control button and the first control button controls release of an inert gas and the second control button controls current delivery to the elongate member.

6. The plasma generator of claim 5, wherein the first control button is configured to supply a burst of fluid or a continuous flow of fluid and further includes a stop feature.

7. The plasma generator of claim 1, wherein the plasma generator is configured to be disposable.

8. The plasma generator of claim 1, wherein the medical device and the plasma generator are configured to be operated using a single hand of a user.

9. The plasma generator of claim 1, wherein the one or more rings comprises a set of snap rings.

10. The plasma generator of claim 1, wherein the elongate member is configured to be located entirely outside of the medical device.

11. The plasma generator of claim 1, wherein the medical device is a debrider.

12. An apparatus comprising:
a debrider; and
a plasma generator configured to be operably connectable to the debrider, wherein the plasma generator comprises:
an elongate member having a distal end, a proximal end, and a lumen extending therethrough, the proximal end configured to be connectable to a source of an inert gas, the elongate member comprising an insulated sheath;
a plasma generation tip disposed at the distal end of the elongate member, the plasma generation tip configured to be in electrical communication with a generator;
an activation switch configured to control generation of plasma at the plasma generation tip; and
a malleable sheath extending proximally from the proximal end of the elongate member, wherein the insulated sheath is encircled at the proximal end by the malleable sheath;
where the plasma generator comprises two or more snap rings configured to removably attach the plasma generator to an exterior portion of the debrider, at least one of the snap rings engageable with the malleable sheath.

13. The apparatus of claim 12, wherein the plasma generator further comprises a first electrode and a second electrode, each of the first and second electrodes extending along the elongate member to the distal end.

14. The apparatus of claim 13, wherein the first electrode is an active electrode and the second electrode is a return electrode.

15. The apparatus of claim 12, wherein the plasma generation tip comprises stainless steel.

16. The apparatus of claim 12, wherein the plasma generator is configured to generate a plasma plume at the plasma generation tip extending between 20 mm and 50 mm in front of a distal end of the plasma generator.

17. The apparatus of claim 12, wherein the plasma generator is configured for non-contact treatment.

18. The apparatus of claim 12, wherein the plasma generator is configured to coagulate blood in the vicinity of the plasma generation tip.

19. The apparatus of claim 12, wherein the plasma generator is configured to perform a disinfection function in the vicinity of the plasma generation tip.

20. The apparatus of claim 12, wherein the activation switch comprises a first control button and a second control button and the first control button is configured to control release of an inert gas and the second control button is configured to control current delivery to the elongate member.

21. The apparatus of claim 12, wherein the debrider and the plasma generator are configured to be operated using a single hand of a user.

\* \* \* \* \*